(12) United States Patent
Spiridigliozzi et al.

(10) Patent No.: US 7,974,845 B2
(45) Date of Patent: *Jul. 5, 2011

(54) STUTTERING TREATMENT METHODS AND APPARATUS

(75) Inventors: John Spiridigliozzi, San Mateo, CA (US); Amir A. Abolfathi, Woodside, CA (US)

(73) Assignee: Sonitus Medical, Inc., San Mateo, CA (US)

( * ) Notice: Subject to any disclaimer, the term of this patent is extended or adjusted under 35 U.S.C. 154(b) by 670 days.

This patent is subject to a terminal disclaimer.

(21) Appl. No.: 12/032,608

(22) Filed: Feb. 15, 2008

(65) Prior Publication Data

US 2009/0210231 A1 Aug. 20, 2009

(51) Int. Cl.
*G10L 15/06* (2006.01)

(52) U.S. Cl. ......... 704/271; 381/151; 381/364; 704/270

(58) Field of Classification Search .................. 704/270, 704/271; 381/151, 364; 600/23
See application file for complete search history.

(56) References Cited

U.S. PATENT DOCUMENTS

| | | | |
|---|---|---|---|
| 2,045,404 A | 6/1936 | Nicholides | |
| 2,161,169 A | 6/1939 | Jefferis | |
| 2,318,872 A | 5/1943 | Madiera | |
| 2,977,425 A | 3/1961 | Cole | |
| 2,995,633 A | 8/1961 | Puharich et al. | |
| 3,156,787 A | 11/1964 | Puharich et al. | |
| 3,170,993 A | 2/1965 | Puharich et al. | |
| 3,267,931 A | 8/1966 | Puharich et al. | |
| 3,325,743 A | 6/1967 | Blum | |
| 3,787,641 A | 1/1974 | Santori | |
| 3,894,196 A | 7/1975 | Briskey | |
| 3,985,977 A | 10/1976 | Beaty et al. | |
| 4,025,732 A | 5/1977 | Traunmuller | |
| 4,150,262 A | 4/1979 | Ono | |
| 4,498,461 A | 2/1985 | Hakansson | |
| 4,591,668 A | 5/1986 | Iwata | |
| 4,612,915 A | 9/1986 | Hough et al. | |
| 4,642,769 A | 2/1987 | Petrofsky | |
| 4,738,268 A | 4/1988 | Kipnis | |
| 4,817,044 A | 3/1989 | Ogren | |

(Continued)

FOREIGN PATENT DOCUMENTS

EP 0715838 A2 6/1996

(Continued)

OTHER PUBLICATIONS

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

(Continued)

*Primary Examiner* — Vincent P Harper
(74) *Attorney, Agent, or Firm* — Levine Bagade Han LLP

(57) ABSTRACT

Stuttering treatment methods and apparatus which utilize removable oral-based appliances having actuators which are attached, adhered, or otherwise embedded into or upon a dental or oral appliance are described. Such oral appliances may receive the user's voice and process the voice to introduce a time delay and/or a frequency shift. The altered audio feedback signal is then transmitted back to the user through a tooth, teeth, or other bone via a vibrating actuator element. The actuator element may utilize electromagnetic or piezoelectric actuator mechanisms and may be positioned directly along the dentition or along an oral appliance housing in various configurations.

19 Claims, 12 Drawing Sheets

U.S. PATENT DOCUMENTS

| | | | |
|---|---|---|---|
| 4,832,033 A | 5/1989 | Maher et al. | |
| 4,920,984 A | 5/1990 | Furumichi et al. | |
| 4,982,434 A | 1/1991 | Lenhardt et al. | |
| 5,012,520 A | 4/1991 | Steeger | |
| 5,033,999 A | 7/1991 | Mersky | |
| 5,047,994 A | 9/1991 | Lenhardt et al. | |
| 5,060,526 A | 10/1991 | Barth et al. | |
| 5,082,007 A | 1/1992 | Adell | |
| 5,233,987 A | 8/1993 | Fabian et al. | |
| 5,323,468 A | 6/1994 | Bottesch | |
| 5,325,436 A | 6/1994 | Soli et al. | |
| 5,372,142 A | 12/1994 | Madsen et al. | |
| 5,402,496 A | 3/1995 | Soli et al. | |
| 5,403,262 A | 4/1995 | Gooch | |
| 5,447,489 A * | 9/1995 | Issalene et al. | 600/25 |
| 5,455,842 A | 10/1995 | Merskey et al. | |
| 5,460,593 A | 10/1995 | Mersky et al. | |
| 5,546,459 A | 8/1996 | Sih et al. | |
| 5,558,618 A | 9/1996 | Maniglia | |
| 5,565,759 A | 10/1996 | Dunstan | |
| 5,616,027 A | 4/1997 | Jacobs et al. | |
| 5,624,376 A | 4/1997 | Ball et al. | |
| 5,661,813 A | 8/1997 | Shimauchi et al. | |
| 5,706,251 A | 1/1998 | May | |
| 5,760,692 A | 6/1998 | Block | |
| 5,800,336 A | 9/1998 | Ball et al. | |
| 5,812,496 A | 9/1998 | Peck | |
| 5,828,765 A | 10/1998 | Gable | |
| 5,902,167 A | 5/1999 | Filo et al. | |
| 5,914,701 A | 6/1999 | Gersheneld et al. | |
| 5,961,443 A | 10/1999 | Rastatter et al. | |
| 5,984,681 A | 11/1999 | Huang | |
| 6,029,558 A | 2/2000 | Stevens et al. | |
| 6,047,074 A | 4/2000 | Zoels et al. | |
| 6,068,590 A | 5/2000 | Brisken | |
| 6,072,884 A | 6/2000 | Kates | |
| 6,072,885 A | 6/2000 | Stockham, Jr. et al. | |
| 6,075,557 A | 6/2000 | Holliman et al. | |
| 6,115,477 A | 9/2000 | Filo et al. | |
| 6,118,882 A | 9/2000 | Haynes | |
| 6,171,229 B1 | 1/2001 | Kroll et al. | |
| 6,223,018 B1 | 4/2001 | Fukumoto et al. | |
| 6,239,705 B1 | 5/2001 | Glen | |
| 6,333,269 B2 | 12/2001 | Naito et al. | |
| 6,377,693 B1 | 4/2002 | Lippa et al. | |
| 6,394,969 B1 | 5/2002 | Lenhardt | |
| 6,504,942 B1 | 1/2003 | Hong et al. | |
| 6,538,558 B2 | 3/2003 | Sakazume et al. | |
| 6,585,637 B2 | 7/2003 | Brillhart et al. | |
| 6,631,197 B1 | 10/2003 | Taenzer | |
| 6,633,747 B1 | 10/2003 | Reiss | |
| 6,682,472 B1 | 1/2004 | Davis | |
| 6,754,472 B1 | 6/2004 | Williams et al. | |
| 6,778,674 B1 | 8/2004 | Panasik et al. | |
| 6,826,284 B1 | 11/2004 | Benesty et al. | |
| 6,885,753 B2 | 4/2005 | Bank | |
| 6,917,688 B2 | 7/2005 | Yu et al. | |
| 6,941,952 B1 | 9/2005 | Rush, III | |
| 6,954,668 B1 | 10/2005 | Cuozzo | |
| 6,985,599 B2 | 1/2006 | Asnes | |
| 7,003,099 B1 | 2/2006 | Zhang et al. | |
| 7,033,313 B2 | 4/2006 | Lupin et al. | |
| 7,035,415 B2 | 4/2006 | Belt et al. | |
| 7,074,222 B2 | 7/2006 | Westerkull | |
| 7,076,077 B2 | 7/2006 | Atsumi et al. | |
| 7,099,822 B2 | 8/2006 | Zangi | |
| 7,162,420 B2 | 1/2007 | Zangi et al. | |
| 7,171,003 B1 | 1/2007 | Venkatesh et al. | |
| 7,171,008 B2 | 1/2007 | Elko | |
| 7,174,022 B1 | 2/2007 | Zhang et al. | |
| 7,206,423 B1 | 4/2007 | Feng et al. | |
| 7,246,058 B2 | 7/2007 | Burnett | |
| 7,258,533 B2 | 8/2007 | Tanner et al. | |
| 7,269,266 B2 | 9/2007 | Anjanappa et al. | |
| 7,271,569 B2 | 9/2007 | Oglesbee | |
| 7,310,427 B2 | 12/2007 | Retchin et al. | |
| 7,329,226 B1 | 2/2008 | Ni et al. | |
| 7,331,349 B2 | 2/2008 | Brady et al. | |
| 7,333,624 B2 | 2/2008 | Husung | |
| 7,361,216 B2 | 4/2008 | Kangas et al. | |
| 7,409,070 B2 | 8/2008 | Pitulia | |
| 7,486,798 B2 | 2/2009 | Anjanappa et al. | |
| 7,520,851 B2 | 4/2009 | Davis et al. | |
| 7,522,738 B2 | 4/2009 | Miller, III | |
| 7,522,740 B2 | 4/2009 | Julstrom et al. | |
| 2001/0003788 A1 | 6/2001 | Ball et al. | |
| 2001/0051776 A1 | 12/2001 | Lenhardt | |
| 2002/0026091 A1 | 2/2002 | Leysieffer | |
| 2002/0071581 A1 | 6/2002 | Leysieffer et al. | |
| 2002/0077831 A1 | 6/2002 | Numa | |
| 2002/0122563 A1 | 9/2002 | Schumaier | |
| 2002/0173697 A1 | 11/2002 | Lenhardt | |
| 2003/0059078 A1 | 3/2003 | Downs et al. | |
| 2003/0091200 A1 | 5/2003 | Pompei | |
| 2003/0212319 A1 | 11/2003 | Magill | |
| 2004/0057591 A1 | 3/2004 | Beck et al. | |
| 2004/0131200 A1 | 7/2004 | Davis | |
| 2004/0141624 A1 | 7/2004 | Davis et al. | |
| 2004/0202339 A1 | 10/2004 | O'Brien, Jr. et al. | |
| 2004/0202344 A1 | 10/2004 | Anjanappa et al. | |
| 2004/0243481 A1 | 12/2004 | Bradbury et al. | |
| 2004/0247143 A1 | 12/2004 | Lantrua et al. | |
| 2005/0037312 A1 | 2/2005 | Uchida | |
| 2005/0067816 A1 | 3/2005 | Buckman | |
| 2005/0070782 A1 | 3/2005 | Brodkin | |
| 2005/0129257 A1 | 6/2005 | Tamura | |
| 2005/0196008 A1 | 9/2005 | Anjanappa et al. | |
| 2005/0241646 A1 | 11/2005 | Sotos et al. | |
| 2006/0008106 A1 | 1/2006 | Harper | |
| 2006/0025648 A1 | 2/2006 | Lupin et al. | |
| 2006/0064037 A1 | 3/2006 | Shalon et al. | |
| 2006/0167335 A1 | 7/2006 | Park et al. | |
| 2006/0270467 A1 | 11/2006 | Song et al. | |
| 2006/0275739 A1 | 12/2006 | Ray | |
| 2007/0010704 A1* | 1/2007 | Pitulia | 600/23 |
| 2007/0036370 A1 | 2/2007 | Granovetter et al. | |
| 2007/0041595 A1 | 2/2007 | Carazo et al. | |
| 2007/0142072 A1 | 6/2007 | Lassally | |
| 2007/0230713 A1 | 10/2007 | Davis | |
| 2007/0242835 A1 | 10/2007 | Davis | |
| 2007/0265533 A1 | 11/2007 | Tran | |
| 2007/0276270 A1 | 11/2007 | Tran | |
| 2007/0280491 A1 | 12/2007 | Abolfathi | |
| 2007/0280492 A1 | 12/2007 | Abolfathi | |
| 2007/0280493 A1 | 12/2007 | Abolfathi | |
| 2007/0280495 A1 | 12/2007 | Abolfathi | |
| 2007/0286440 A1 | 12/2007 | Abolfathi et al. | |
| 2007/0291972 A1 | 12/2007 | Abolfathi et al. | |
| 2008/0019542 A1 | 1/2008 | Menzel et al. | |
| 2008/0019557 A1 | 1/2008 | Bevirt et al. | |
| 2008/0021327 A1 | 1/2008 | El-Bialy et al. | |
| 2008/0064993 A1 | 3/2008 | Abolfathi et al. | |
| 2008/0070181 A1 | 3/2008 | Abolfathi et al. | |
| 2008/0304677 A1 | 12/2008 | Abolfathi et al. | |
| 2009/0022351 A1* | 1/2009 | Wieland et al. | 381/364 |
| 2009/0028352 A1 | 1/2009 | Petroff | |
| 2009/0052698 A1 | 2/2009 | Rader et al. | |
| 2009/0088598 A1 | 4/2009 | Abolfathi | |
| 2009/0097684 A1 | 4/2009 | Abolfathi et al. | |
| 2009/0097685 A1 | 4/2009 | Menzel et al. | |
| 2009/0099408 A1 | 4/2009 | Abolfathi et al. | |
| 2009/0105523 A1 | 4/2009 | Kassayan et al. | |
| 2009/0147976 A1 | 6/2009 | Abolfathi | |
| 2009/0149722 A1 | 6/2009 | Abolfathi et al. | |
| 2009/0180652 A1 | 7/2009 | Davis et al. | |

FOREIGN PATENT DOCUMENTS

| | | | |
|---|---|---|---|
| EP | 0741940 A1 | 11/1996 | |
| EP | 0824889 A1 | 2/1998 | |
| EP | 1299052 A1 | 2/2002 | |
| EP | 1633284 A1 | 12/2004 | |
| EP | 1691686 A1 | 8/2006 | |
| EP | 1718255 A1 | 11/2006 | |
| EP | 1783919 A1 | 5/2007 | |
| JP | 2007028248 A2 | 2/2007 | |
| JP | 2007028610 A2 | 2/2007 | |
| JP | 2007044284 A2 | 2/2007 | |

| | | |
|---|---|---|
| JP | 2007049599 A2 | 2/2007 |
| JP | 2007049658 A2 | 2/2007 |
| WO | WO 83/02047 | 6/1983 |
| WO | WO 91/02678 | 3/1991 |
| WO | WO 95/19678 | 7/1995 |
| WO | WO 96/21335 | 7/1996 |
| WO | WO 02/09622 | 2/2002 |
| WO | WO 2004/045242 | 5/2004 |
| WO | WO 2004/105650 | 12/2004 |
| WO | WO 2005/000391 | 1/2005 |
| WO | WO 2005/037153 | 4/2005 |
| WO | WO 2005/053533 | 6/2005 |
| WO | WO 2006/088410 | 8/2006 |
| WO | WO 2006/130909 | 12/2006 |
| WO | WO 2007/043055 | 4/2007 |
| WO | WO 2007/052251 | 5/2007 |
| WO | WO 2007/059185 | 5/2007 |
| WO | WO 2007/140367 | 12/2007 |
| WO | WO 2007/140368 | 12/2007 |
| WO | WO 2007/140373 | 12/2007 |
| WO | WO 2007/143453 | 12/2007 |
| WO | WO 2008/024794 | 2/2008 |
| WO | WO 2008/030725 | 3/2008 |
| WO | WO 2009/014812 | 1/2009 |
| WO | WO 2009/025917 | 2/2009 |
| WO | WO 2009/066296 | 5/2009 |

OTHER PUBLICATIONS

Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org.

Berard, G., "Hearing Equals Behavior" [summary], 1993, http://www.bixby.org/faq/tinnitus/treatment.html.

Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.

Dental Cements—Premarket Notification, U.S. Department of Health and Human Services Food and Drug Administration Center for Devices and Radiological Health, pp. 1-10, Aug. 18, 1998.

Henry, et al. "Comparison of Custom Sounds for Achieving Tinnitus Relief," *J Am Acad Audiol*,15:585.598, 2004.

Jastreboff, Pawel, J., "Phantom auditory perception (tinnitus): mechanisms of generation and perception," *Neuroscience Research*, 221-254, 1990, Elsevier Scientific Publishers Ireland, Ltd.

Robb, "Tinnitus Device Directory Part I," *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9), 2021-2033, Sep. 2007.

Stuart, A., et al., "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

U.S. Appl. No. 11/672,239, filed Feb. 7, 2007 in the name of Abolfathi, Non-final Office Action mailed Jun. 18, 2009.

U.S. Appl. No. 11/672,239, filed Feb. 7, 2007 in the name of Abolfathi, Non-final Office Action mailed Nov. 13, 2008.

U.S. Appl. No. 11/672,250, filed Feb. 7, 2007 in the name of Abolfathi, Non-final Office Action mailed Apr. 21, 2009.

U.S. Appl. No. 11/672,250, filed Feb. 7, 2007 in the name of Abolfathi, Non-final Office Action mailed Aug. 8, 2008.

U.S. Appl. No. 11/672,264, filed Feb. 7, 2007 in the name of Abolfathi, Non-Final Rejection mailed Apr. 28, 2009.

U.S. Appl. No. 11/672,264, filed Feb. 7, 2007 in the name of Abolfathi, Non-Final Rejection mailed Aug. 6, 2008.

U.S. Appl. No. 11/672,271, filed Feb. 7, 2007 in the name of Abolfathi, Final Office Action mailed May 18, 2009.

U.S. Appl. No. 11/672,271, filed Feb. 7, 2007 in the name of Abolfathi, Non-final Office Action mailed Aug. 20, 2008.

U.S. Appl. No. 11/741,648, filed Apr. 27, 2007 in the name of Menzel et al., Final Office Action mailed May 18, 2009.

U.S. Appl. No. 11/741,648, filed Apr. 27, 2007 in the name of Menzel et al., Non-final Office Action mailed Sep. 4, 2008.

U.S. Appl. No. 11/754,823, filed May 29, 2007 in the name of Abolfathi et al., Final Office Action mailed May 12, 2009.

U.S. Appl. No. 11/754,823, filed May 29, 2007 in the name of Abolfathi et al., Non-final Office Action mailed Aug. 14, 2008.

U.S. Appl. No. 11/754,833, filed May 29, 2007 in the name of Abolfathi et al., Final Office Action mailed May 14, 2009.

U.S. Appl. No. 11/754,833, filed May 29, 2007 in the name of Abolfathi et al., Non-final Office Action mailed Aug. 6, 2008.

U.S. Appl. No. 11/866,345, filed May 29, 2007 in the name of Abolfathi et al., Final Office Action mailed Apr. 15, 2009.

U.S. Appl. No. 11/866,345, filed May 29, 2007 in the name of Abolfathi et al., Non-final Office Action mailed Mar. 19, 2008.

Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

\* cited by examiner

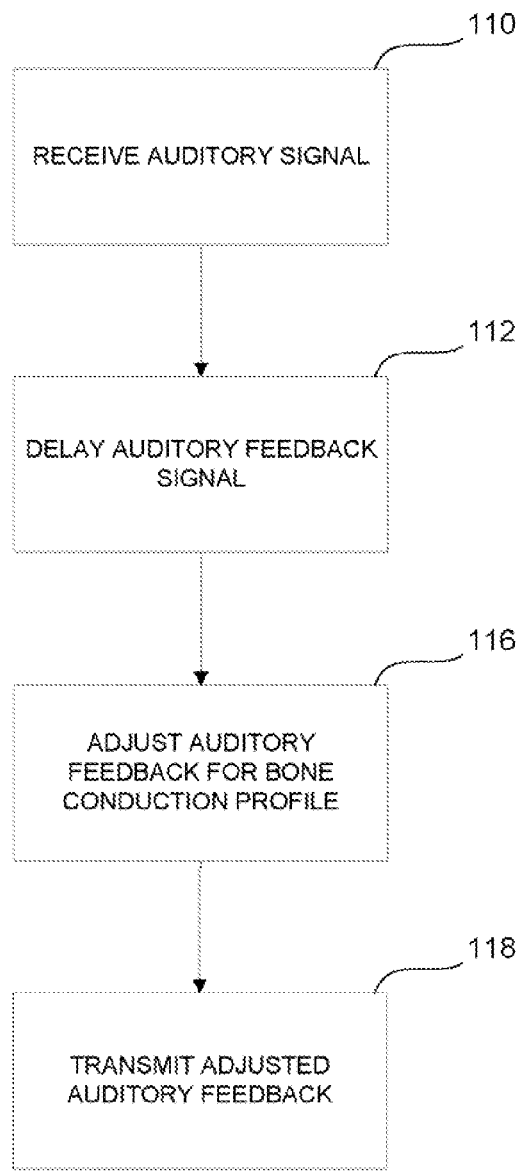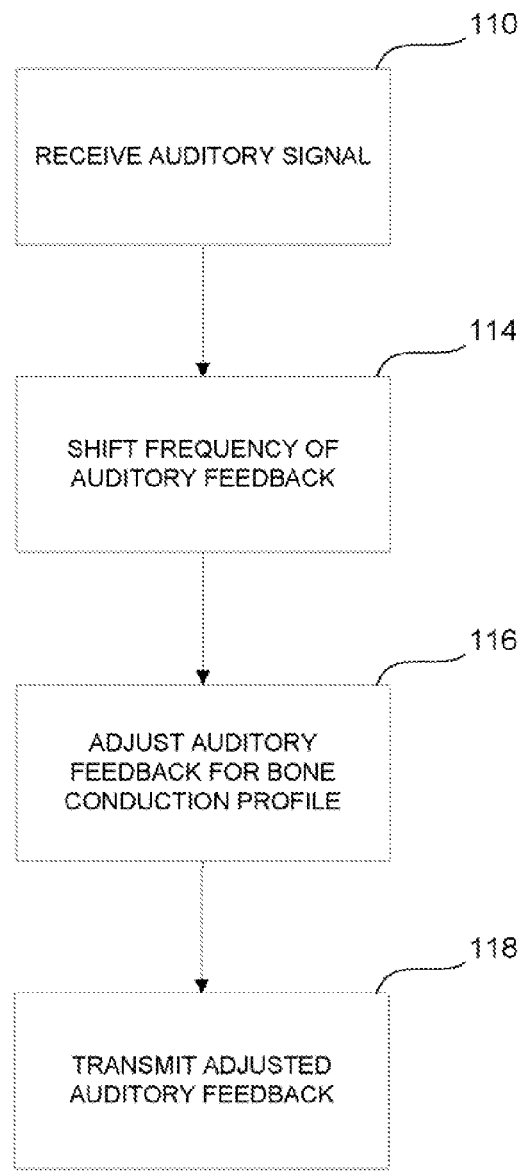
FIG. 11A
FIG. 11B

STUTTERING TREATMENT METHODS AND APPARATUS

FIELD OF THE INVENTION

The present invention relates to methods and apparatus for treating stuttering via altered auditory feedback. More particularly, the present invention relates to methods and apparatus for treating stuttering by transmitting a user's voice which has been altered via bone conduction through teeth or bone structures in and/or around the mouth.

BACKGROUND OF THE INVENTION

The causes of stuttering are not fully understood but researchers believe that it may be caused by interference between the left and right hemispheres of the brain competing against one another to send signals to the muscles used to produce speech. These conflicting signals ultimately impair the muscles resulting in stuttering, which is typically characterized by interruptions in speech flow, repetitions, prolongations, and pauses in speech.

The treatments for stuttering are varied and include methods such as psychological therapy, drug, therapy, and altered auditory feedback (AAF). Most AAF treatments can be divided into three categories: delayed auditory feedback (DAF), frequency-shifted auditor, feedback (FAF), and masked auditory feedback (MAF). Treatment using DAF typically utilizes a user's own voice which is delayed between 50 to 200 ms and then relayed back to the user, usually through headphones or an earpiece. This type of treatment relies on the "choral effect", which occurs when people who stutter speak or sing in unison with others, experience a dramatic reduction or even elimination of stuttering.

Treatments using FAF are based on changing the frequency characteristics of the user's voice by, about a half octave such that the relayed auditory feedback sounds somewhat distorted to the speaker. This frequency shift is believed to effect the user's brain in the same manner as DAF treatment. The MAF treatment involves generating a synthetic sine signal corresponding to the user's own phonetic frequency and relaying this masking feedback to the user.

These treatments usually involve placing a device within the ear canal of the user to completely or partially obstruct the opening much like air-conduction hearing aids. However, such devices are intended to be left in place even when the user is not talking and will also obstruct ambient noises that the user may wish to hear. Moreover, such in-ear devices (as well as other external devices) are usually visible to others and may thus be a deterrent for use by some users for aesthetic reasons. Other devices utilizing such treatments are placed upon a post which is permanently implanted into the skull of the user. However, such devices require invasive surgery and present various complications which may occur as a result.

Accordingly, there exists a need for methods and apparatus for receiving and processing a user's voice and effectively transmitting these processed signals back to the user with minimal obstruction.

SUMMARY OF THE INVENTION

An electronic device may be attached, adhered, or otherwise embedded into or upon a removable dental or oral appliance to form an assembly which may conduct audio signals to a user via vibratory conduction through bone. Such a removable oral appliance may be a custom-made device fabricated from a thermal forming process utilizing a replicate model of a dental structure obtained by conventional dental impression methods. The electronic assembly may receive incoming sounds either directly or through a receiver to process and amplify the signals and transmit the processed sounds via a vibrating actuator element coupled to a tooth or other bone structure, such as the maxillary, mandibular, or palatine bone structure.

In using an oral appliance assembly, the oral appliance may utilize altered auditory feedback (AAF) for the treatment of stuttering. Accordingly, in one example of treating stuttering via delayed auditory feedback (DAF) and/or frequency-shifted auditory feedback (FAF), the user's own voice may be received via a microphone located upon the oral assembly or separately from the oral appliance. The user's voice may then be processed such that the voice data is delayed by about, e.g., 60 ms. The delay in the auditory feedback may alternatively range anywhere from about 50 ms to 200 ms.

In addition to delaying the auditory feedback, the auditory feedback signal may also be shifted in frequency by about, e.g., +500 Hz. In other variations, the frequency may be shifted anywhere from less than a half octave to a full octave or more, depending upon the desired results. With the auditor, feedback delayed and shifted in frequency, the signal may be further adjusted or equalized to account for the user's particular bone conduction profile, which may be obtained utilizing standard bone conduction measurements. Accounting for the user's bone conduction profile, particularly through the skull, may facilitate optimization of the altered auditory feedback signal by adjusting particular frequencies or adjusting amplitude or gain such that the vibrationally conducted altered feedback signal reaches the user's middle and/or inner ear with minimal loss.

Once the altered feedback signal has been appropriately adjusted for delay, frequency, bone conduction, etc., it may be vibrationally transmitted via the removable oral appliance through the user's tooth or teeth or other bone structure such as the palatal or mandibular bone, etc. Thus, as the user speaks their voice is sampled and adjusted, as described above, and then retransmitted via the removable oral appliance to effect AAF treatment and to reduce or eliminate stuttering.

The assembly for transmitting vibrations via at least one tooth may generally comprise a housing having a shape which is conformable to at least a portion of the at least one tooth, and an actuator disposed within or upon the housing and in vibratory communication with a surface of the at least one tooth. Moreover, the actuator itself may be a separate assembly from the electronics and may be positioned along another surface of the tooth, such as the occlusal surface, or even attached to an implanted post or screw embedded into the underlying bone.

The actuator utilized in the actuator assembly may be an electromagnetic or piezoelectric actuator. Piezoelectric transducers in particular may be used in various configurations due in part to the various vibrational modes which may be utilized to transmit the acoustic signals as vibrations through a tooth or teeth. Any number of actuator may be utilized for particular applications. For instance, low voltage multi-layer piezoelectric actuator manufactured by Morgan Electro Ceramics Ltd. (Wrexham, England) may be utilized for the applications described herein.

Aside from actuator and housing assemblies which are positioned along or against one or more teeth, actuator assemblies may be alternatively mounted along a retainer-like structure configured for placement adjacent or along the palate of the user. An arch may extend between coupling portions which are configured to extend from the arch for placement against the lingual surfaces of teeth on opposite sides of the user's dentition. Rather than utilizing actuator assemblies directly upon the teeth, the actuator may be removably or permanently integrated along the arch such that elongational vibration of the actuator conducts the vibrations along the arch for transmission through the coupling portions and into the user's teeth. Alternatively, one or more actuators may be positioned along the arch and actuated to directly conduct vibrations through the user's palatal bone.

BRIEF DESCRIPTION OF THE DRAWINGS

FIGS. 11A and 11B illustrate flow charts for alternative treatments for altering the user's voice for retransmission back to the user.

DETAILED DESCRIPTION OF THE INVENTION

In treating stuttering, methods and apparatus may utilize altered auditory feedback (AAF) treatments. For instance, the most commonly used treatments may include use of delayed auditory feedback (DAF) and/or frequency-shifted auditor) feedback (FAF). A user's own voice may be modified by delaying the retransmission of the voice back to the user and the voice may also be modified in frequency prior to its retransmission. Rather than utilizing an in-ear device, which obstructs the ear canal, or a device which is coupled to a post implanted in the user, the user's voice may be processed and transmitted via bone conduction through an unobstructive and removable oral appliance.

The removable oral appliance may contain an electronic and actuator device attached, adhered, or otherwise embedded into or upon the oral appliance or other oral device to form an assembly which may conduct audio signals to the user via vibratory, conduction through bone. Such an oral appliance may be a custom-made device fabricated from a thermal forming, process utilizing a replicate model of a dental structure obtained by conventional dental impression methods. The electronic and actuator assembly may receive incoming sounds, such as the user's own voice, either directly or through a receiver to process and amplify the signals and transmit the processed sounds via a vibrating actuator element coupled to a tooth or other bone structure, such as the maxillary, mandibular, or palatine bone structure.

Detailed examples and descriptions of the oral appliance and methods of use are more full), described in the following U.S. patent application Ser. Nos. 11/672,239 filed Feb. 7, 2007; 11/741,648 filed Apr. 27, 2007; and 11/754,823 and 11/754,833 both filed May 29, 2007. Each of these applications is incorporated herein by reference in its entirety.

Figure 1:
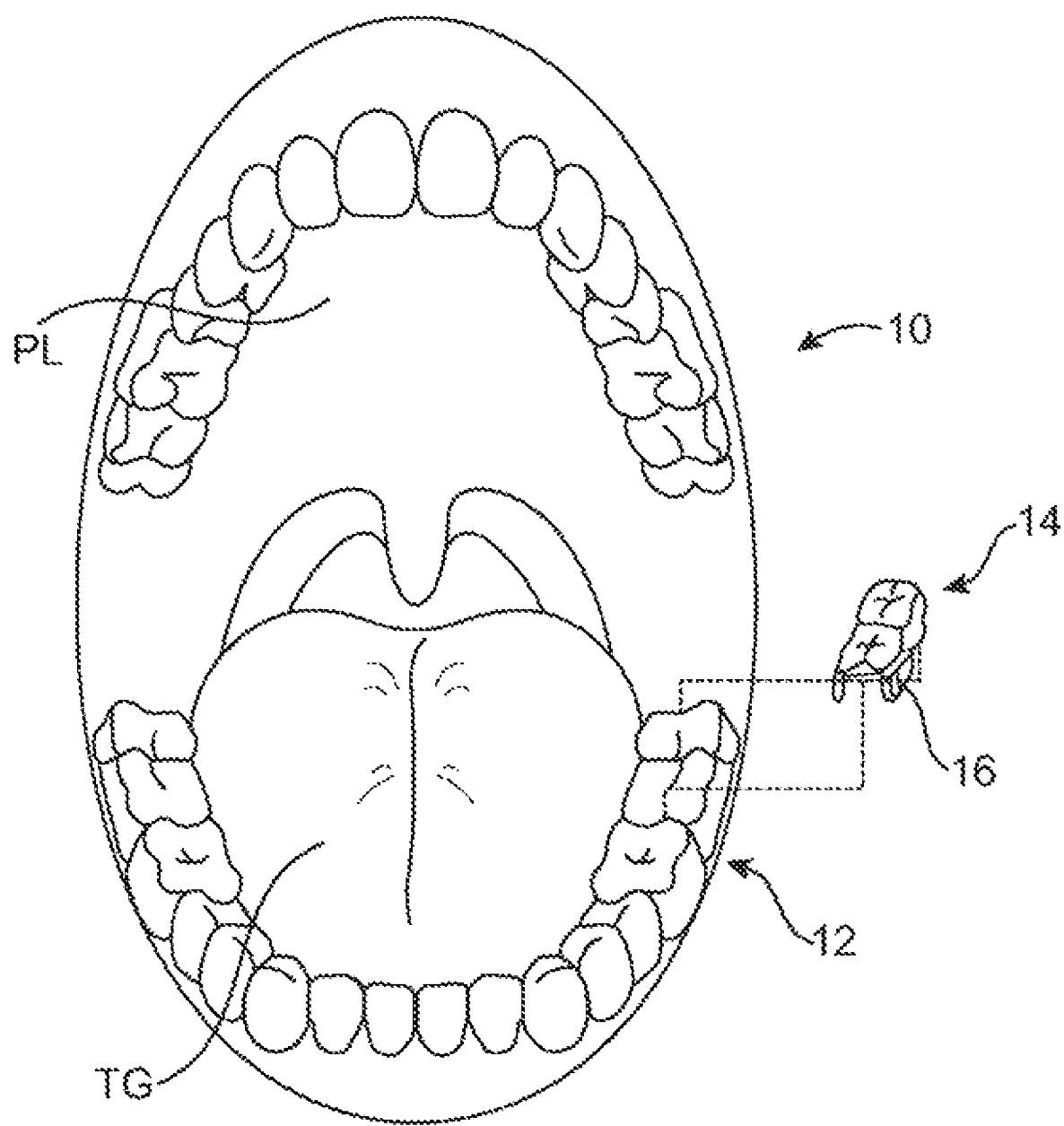
FIG. 1 illustrates the dentition of a patient's teeth and one variation of an oral appliance which is removably placed upon or against the patient's tooth or teeth.

As shown in FIG. 1, a patient's mouth and dentition 10 is illustrated showing one possible location for removably attaching the oral appliance assembly 14 upon or against at least one tooth, such as a molar 12. The patient's tongue TG and palate PL are also illustrated for reference. An electronics and/or actuator assembly 16 may be attached, adhered, or otherwise embedded into or upon the assembly 14, as described below in further detail.

Figure 2A:
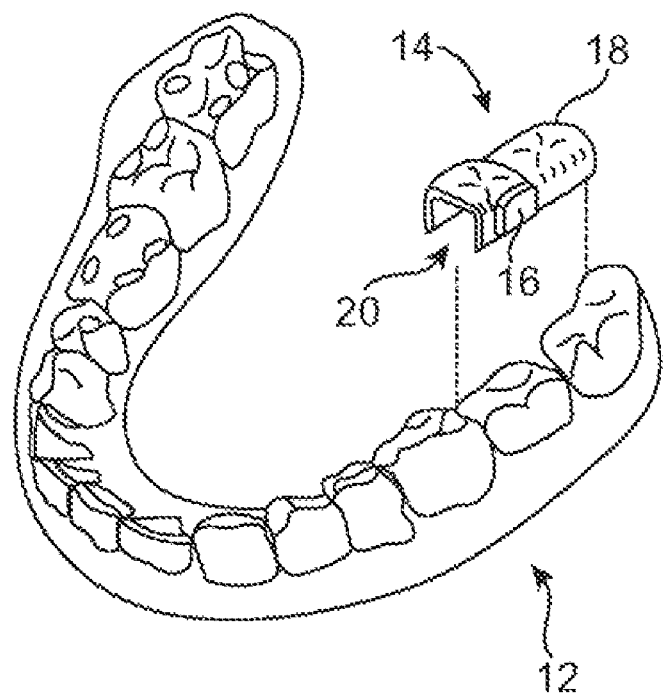
FIG. 2A illustrates a perspective view of the lower teeth showing one exemplary location for placement of the removable oral appliance.

FIG. 2A shows a perspective view of the patient's lower dentition illustrating the assembly 14 comprising a removable oral appliance 18 and the electronics and/or actuator assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or actuator assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein.

Figure 2B:
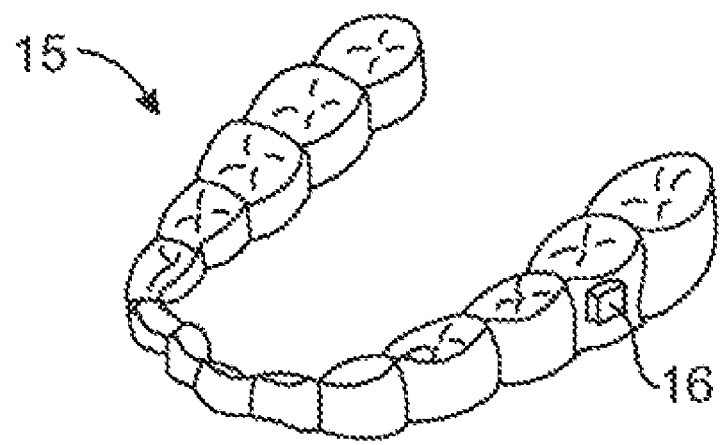
FIG. 2B illustrates another variation of the removable oral appliance in the form of an appliance which is placed over an entire row of teeth in the manner of a mouthguard.

FIG. 2B shows another variation of a removable oral appliance in the form of an appliance 15 which is placed over an entire row of teeth in the manner of a mouthguard. In this variation, appliance 15 may be configured to cover an entire bottom row of teeth or alternatively an entire upper row of teeth. In additional variations, rather than covering the entire rows of teeth, a majority of the row of teeth may be instead be covered by appliance 15. Assembly 16 may be positioned along one or more portions of the oral appliance 15.

Figure 2C:
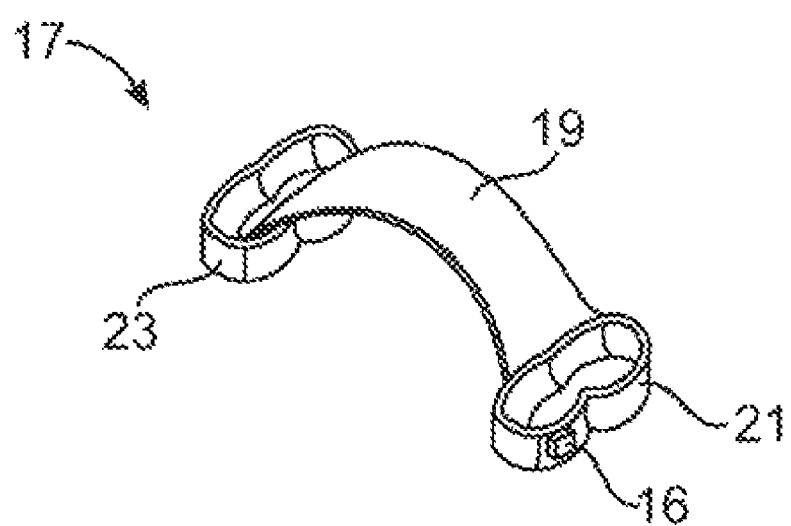
FIG. 2C illustrates another variation of the removable oral appliance which is supported byes arch.

FIG. 2C shows yet another variation of an oral appliance 17 having an arched configuration. In this appliance, one or more tooth retaining portions 21, 23, which in this variation may be placed along the upper row of teeth, may be supported by an arch 19 which may lie adjacent or along the palate of the user. As shown, electronics and/or actuator assembly 16 may be positioned along one or more portions of the tooth retaining portions 21, 23. Moreover, although the variation shown illustrates an arch 19 which may cover only a portion of the palate of the user, other variations may be configured to have an arch which covers the entire palate of the user.

Figure 2D:
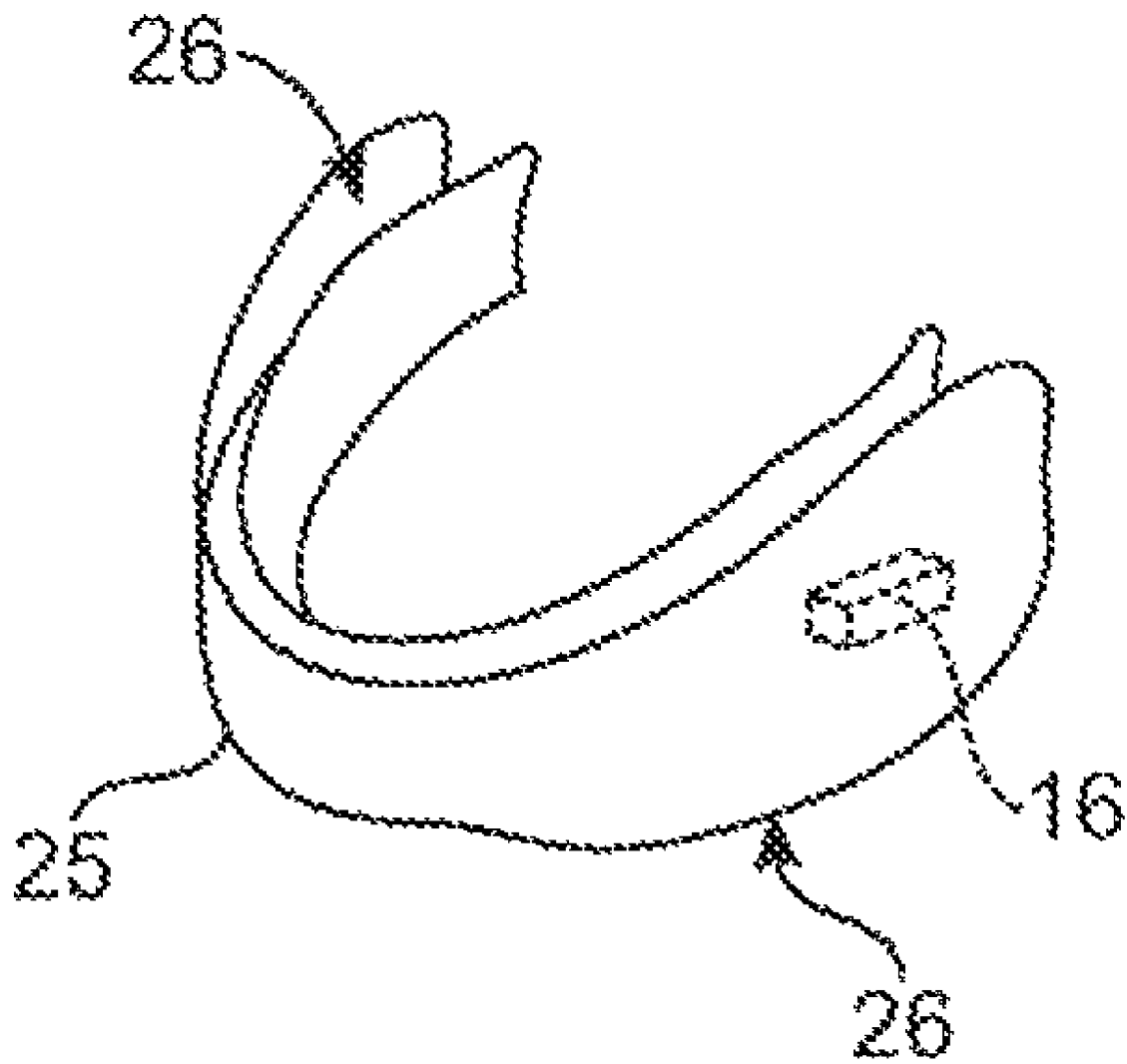
FIG. 2D illustrates another variation of all oral appliance configured as a mouthguard.

FIG. 2D illustrates yet another variation of all oral appliance in the form of a mouthguard or retainer 25 which may be inserted and removed easily from the user's mouth. Such a mouthguard or retainer 25 may be used in sports where conventional mouthguards are worn; however, mouthguard or retainer 25 having assembly 16 integrated therein may be utilized by persons, stutterers, hearing impaired or otherwise, who may simply hold the mouthguard or retainer 25 via grooves or channels 26 between their teeth for receiving instructions remotely and communicating over a distance.

Generally, the volume of electronics and/or actuator assembly 16 may be minimized so as to be unobtrusive and comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g. stereolithography apparatus (SLA), selective laser sintering (SLS), and/or other similar processes utilizing three-dimensional geometry of the patient's dentition, which may be obtained via any number of techniques. Such techniques may include use of scanned dentition using intra-oral scanners such as laser, white light, ultrasound, mechanical three-dimensional touch scanners, magnetic resonance imaging (MRI), computed tomography (CT), other optical methods, etc. Examples for manufacturing the oral appliance are described in further detail in U.S. patent application Ser. No. 11/841,477 filed Aug. 20, 2007, which is incorporated herein by reference in its entirety.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the actuator assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth is the appliance, 18 may have a resulting size slightly smaller than the scanned tooth or teeth upon which the appliance 18 was formed. The fitting, may result in a secure interference fit between the appliance 18 and underlying dentition.

Figure 3:
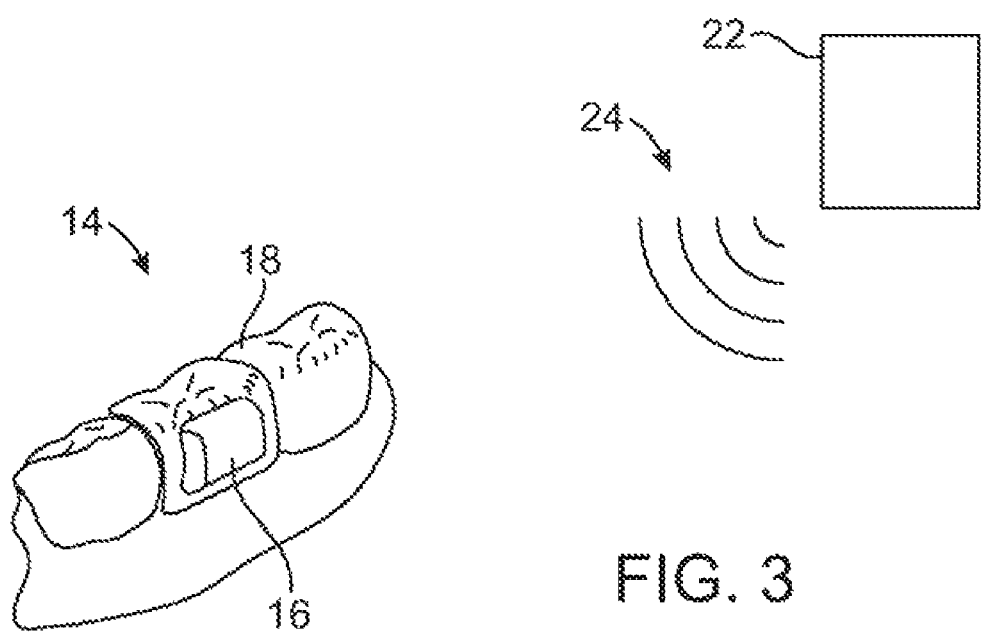
FIG. 3 illustrates a detail perspective view of the oral appliance positioned upon the patient's teeth utilizable in combination with a transmitting assembly external to the mouth and wearable by the patient in another variation of the device.

In one variation, with assembly 14 positioned upon the teeth, as shown in FIG. 3, an extra-buccal transmit ter assembly 22 located outside the patient's mouth may be utilized to receive auditory signals for processing and transmission via a wireless signal 24 to the electronics and/or actuator assembly 16 positioned within the patient's mouth, which may then process and transmit the processed auditory signals via vibratory conduction to the underlying tooth and consequently: to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 4:
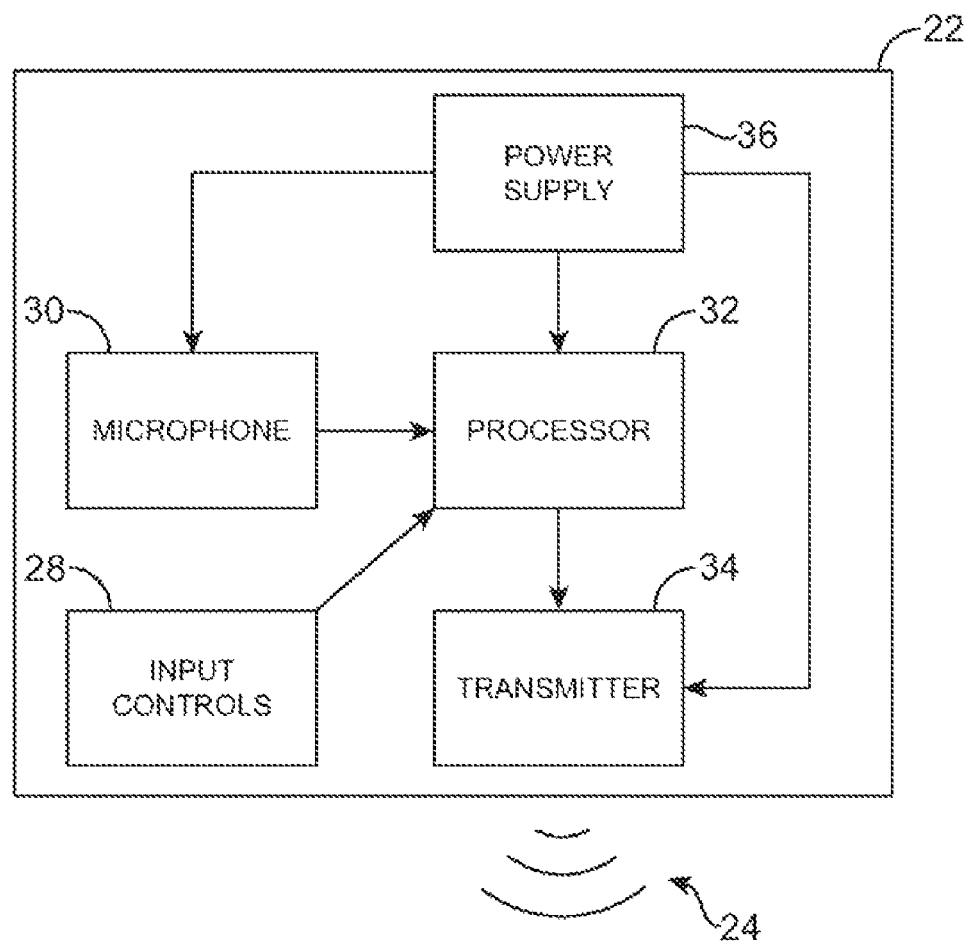
FIG. 4 shows an illustrative configuration of one variation of the individual components of the oral appliance device having an external transmitting assembly with a receiving and actuator assembly within the mouth.
Figure 4:
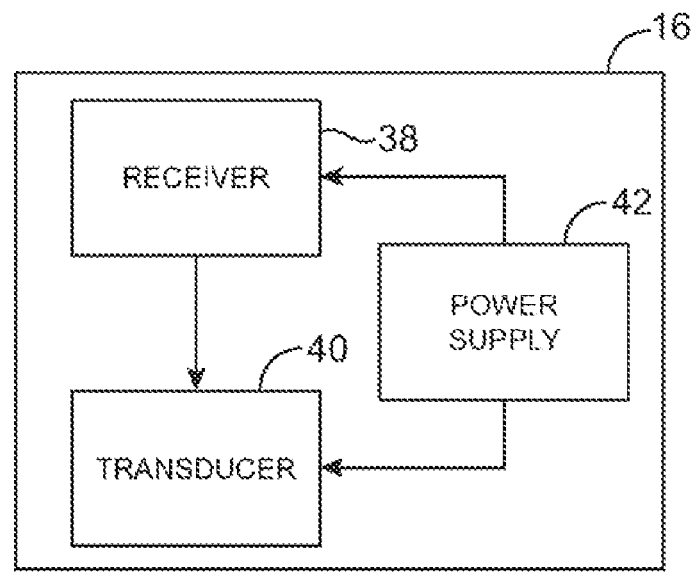

FIG. 4 illustrates a schematic representation of one variation of oral appliance assembly 14 utilizing an extra-buccal transmitter assembly 22, which may generally comprise microphone or microphone array 30 (referred to "microphone 30" for simplicity) for receiving sounds and which is electrically connected to processor 32 for processing the auditory signals. Processor 32 may be connected electrically to transmitter 34 for transmitting the processed signals to the electronics and/or actuator assembly 16 disposed upon or adjacent to the user's teeth. The microphone 30 and processor 32 may be configured to detect and process auditory signals in any practicable range, but may be configured in one variation to detect auditory signals ranging from, e.g., 50 Hertz to 20000 Hertz.

With respect to microphone 30, a variety of various microphone systems may be utilized. For instance, microphone 30 mat be a digital, analog, and/or directional type microphone. Such various types of microphones may be interchangeably configured to be utilized with the assembly, if so desired. Moreover, various configurations and methods for utilizing multiple microphones within the user's mouth may also be utilized, as further described below.

Power supply 36 may be connected to each of the components in transmitter assembly 22 to provide power thereto. The transmitter signals 24 may be in any wireless form utilizing, e.g. radio frequency, ultrasound, microwave. Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or actuator assembly 16, such as acoustic focusing, volume control, filtration, muting, frequency optimization, sound adjustments, and tone adjustments, etc.

The signals transmitted 24 by transmitter 34 may be received by electronics and/or actuator assembly 16 via receiver 38, which may be connected to an internal processor for additional processing of the received signals. The received signals may be communicated to actuator 40, which may vibrate correspondingly against a surface of the tooth to conduct the vibratory signals through the tooth and bone and subsequently to, the middle ear to facilitate hearing of the user. Actuator 40 may be configured as any number of different vibratory mechanisms. For instance, in one variation, actuator 40 may be an electromagnetically actuated actuator. In other variations, actuator 40 may be in the form of a piezoelectric crystal having a range of vibratory frequencies, e.g., between 250 to 15,000 Hz.

Power supply 42 may also be included with assembly 16 to provide power to the receiver, actuator, and/or processor, if also included. Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism such as an internal pendulum or slidable electrical inductance charger as known in the art, which is actuated via. e.g., motions of the jaw and/or movement for translating the mechanical motion into stored electrical energy for charging power supply 42.

Figure 5:
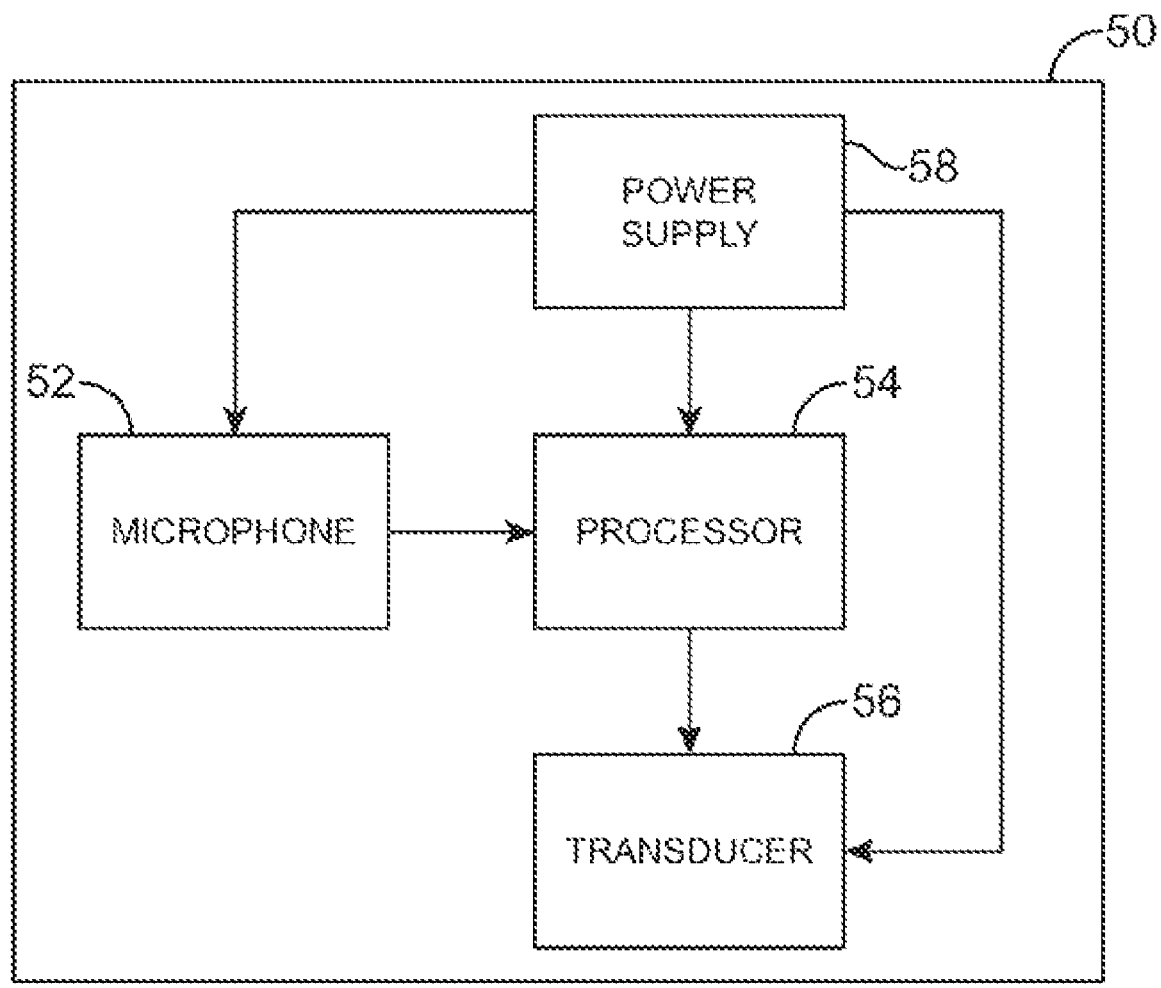
FIG. 5 shows an illustrative configuration of another variation of the device in which the entire assembly is contained by the oral appliance within the user's mouth.

In another variation of assembly 16, rather than utilizing an extra-buccal transmitter, hearing aid assembly 50 may be configured as an independent assembly contained entirely within the user's mouth, as shown in FIG. 5. Accordingly, assembly 50 may include at least one internal microphone 52 in communication with an on-board processor 54. Internal microphone 52 may comprise any number of different types of microphones, as described below in further detail. At least one processor 54 may be used to process any received auditory signals for filtering and/or amplifying the signals and transmitting them to actuator 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secures mechanical contact between the actuator and the tooth is ideally maintained to ensure efficient vibratory communication. Accordingly, any number of mechanisms may be utilized to maintain this vibratory communication.

Figure 6:
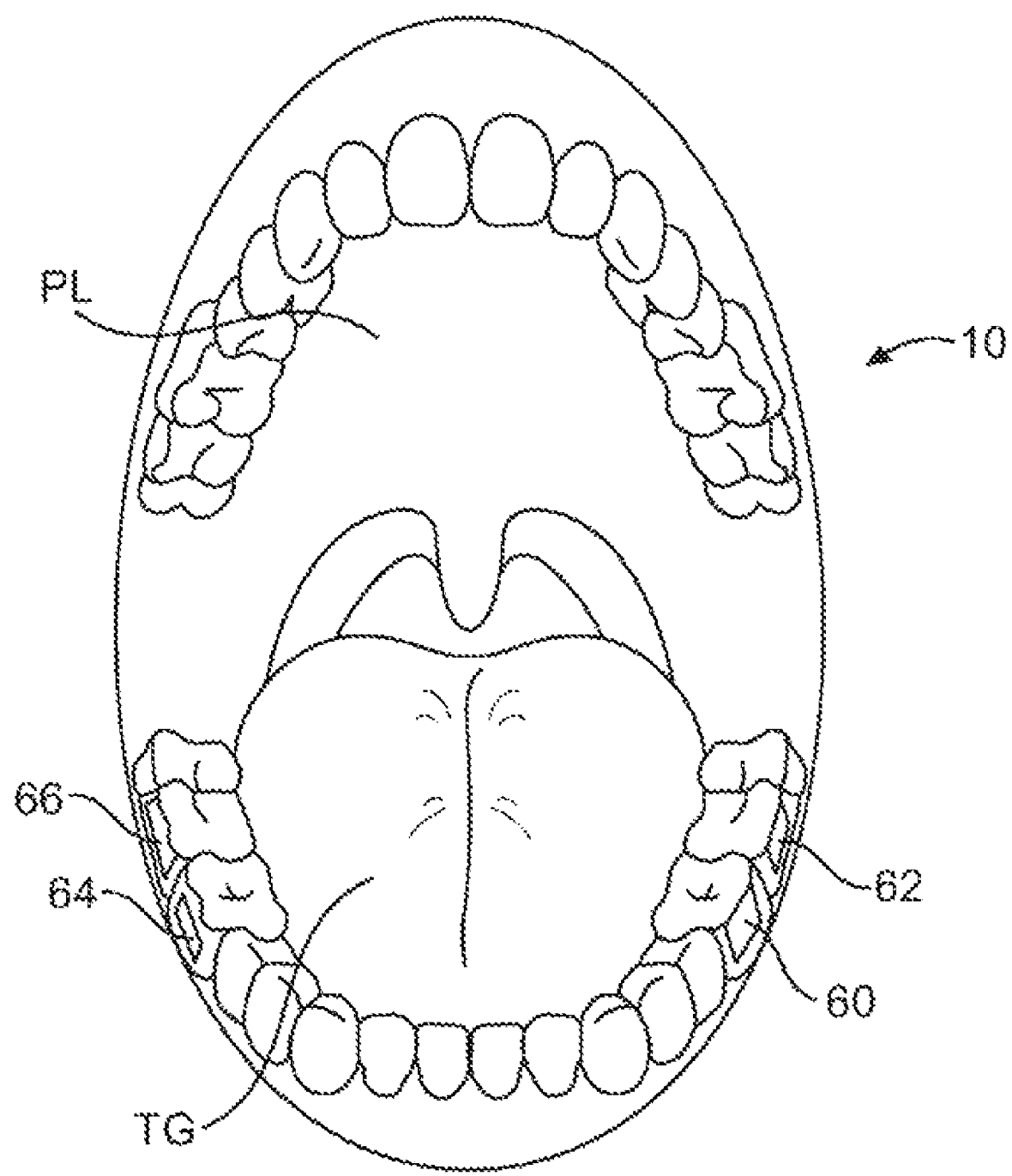
FIG. 6 illustrates an example of low multiple oral appliance assemblies or actuators may be placed on multiple teeth throughout the patient's mouth.

For any of the variations described above, they may be utilized as a single device or in combination with any other variation herein as practicable, to achieve the desired hearing level in the user. Moreover, more than one oral appliance device and electronics and/or actuator assemblies may be utilized at any one time. For example, FIG. 6 illustrates one example where multiple actuator-assemblies 60, 62, 64, 66 may be placed on multiple teeth. Although shown oil the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within overlapping or non-overlapping frequency ranges between each assembly. As mentioned above, each actuator 60, 62, 64, 66 can be programmed or preset for a different frequency response such that each actuator may be optimized for a different frequency response and/or transmission to deliver a relatively high-fidelity sound to the user.

Moreover, each of the different actuators 60, 62, 64, 66 can also be programmed to vibrate in a manner which indicates the directionality of sound received by the microphone worn by the user. For example, different actuators positioned at different locations within the user's mouth can vibrate in a specified manner by providing sound or vibrational queues to inform the user which direction a sound was detected relative to an orientation of the user, as described in further detail below. For instance, a first actuator located. e.g., on a user's left tooth, can be programmed to vibrate for sound detected originating from the user's left side. Similarly, a second actuator located. e.g., on a user's right tooth, can be programmed to vibrate for sound detected originating from the user's right side. Other variations and queues may be utilized as these examples are intended to be illustrative of potential variations.

Figure 7:
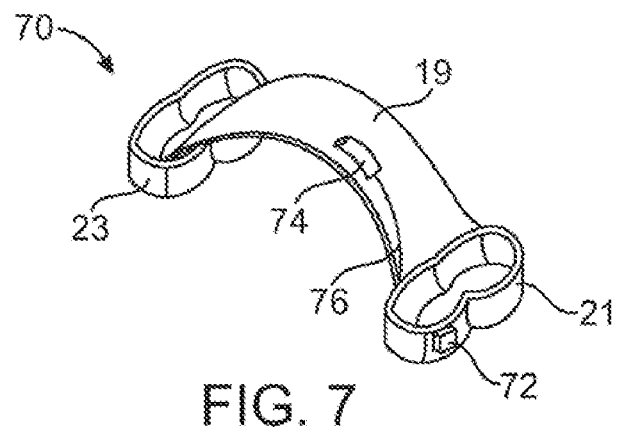
FIG. 7 illustrates another variation of a removable oral appliance supported by an arch and having a microphone unit integrated within the arch.

FIG. 7 illustrates another variation 70 which utilizes an arch 19 connecting one or more tooth retaining portions 21, 23, as described above. However, in this variation, the microphone unit 74 may be integrated within or upon the arch 19 separated from the actuator assembly 72. One or more wires 76 routed through arch 19 may electrically connect the microphone unit 74 to the assembly 72. Alternatively, rather than utilizing a wire 76, microphone unit 74 and assembly 72 may be wirelessly coupled to one another, as described above.

Figure 8A:
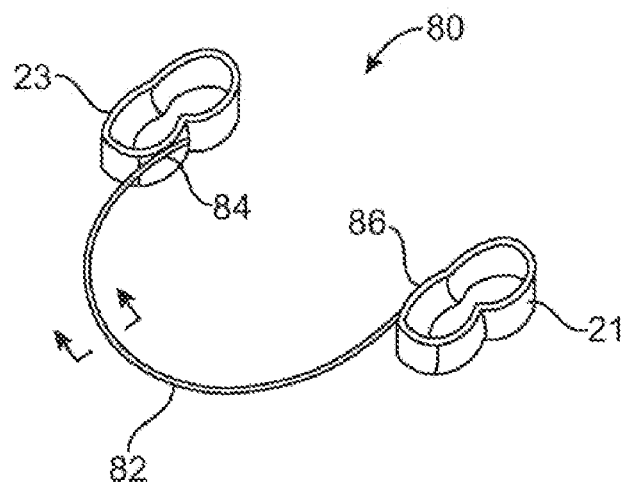
FIG. 8A illustrates another variation of the removable oral appliance supported by a connecting member which may be positioned along the lingual or buccal surfaces of a patient's row of teeth.
Figure 8B:
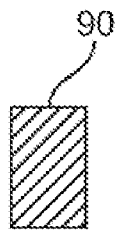
FIGS. 8B to 8E show examples of various cross-sections of the connecting support member of the appliance of FIG. 8A.
Figure 8C:
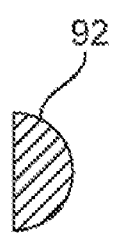
Figure 8D:
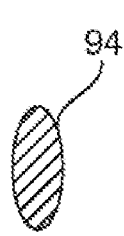
Figure 8E:
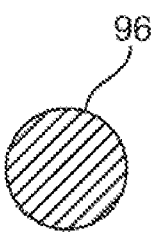

FIG. 8A shows another variation 80 which utilizes a connecting member 82 which may be positioned along the lingual or buccal surfaces of a patient's row of teeth to connect one or more tooth retaining portions 21, 23. Connecting member 82 mat be fabricated from any number of nontoxic materials, such stainless steel, Platinum, etc. and affixed or secured 84, 86 to each respective retaining portions 21, 23. Moreover, connecting member 82 may be shaped to be as non-obtrusive to the user as possible. Accordingly, connecting member 82 may be configured to have a relatively low-profile for placement directly against the lingual or buccal teeth surfaces. The cross-sectional area of connecting member 82 may be configured in any number of shapes so long as the resulting, geometry is non-obtrusive to the user. FIG. 8B illustrates one variation of the cross-sectional area which may be configured as a square or rectangle 90. FIG. 8C illustrates another connecting member geometry configured as a semi-circle 92 where the flat portion may be placed against the teeth surfaces. FIGS. 8D and 8E illustrate other alternative shapes such as an elliptical shape 94 and circular shape 96. These variations are intended to be illustrative and not limiting as other shapes and geometries, as practicable, are intended to be included within this disclosure.

Figure 9:
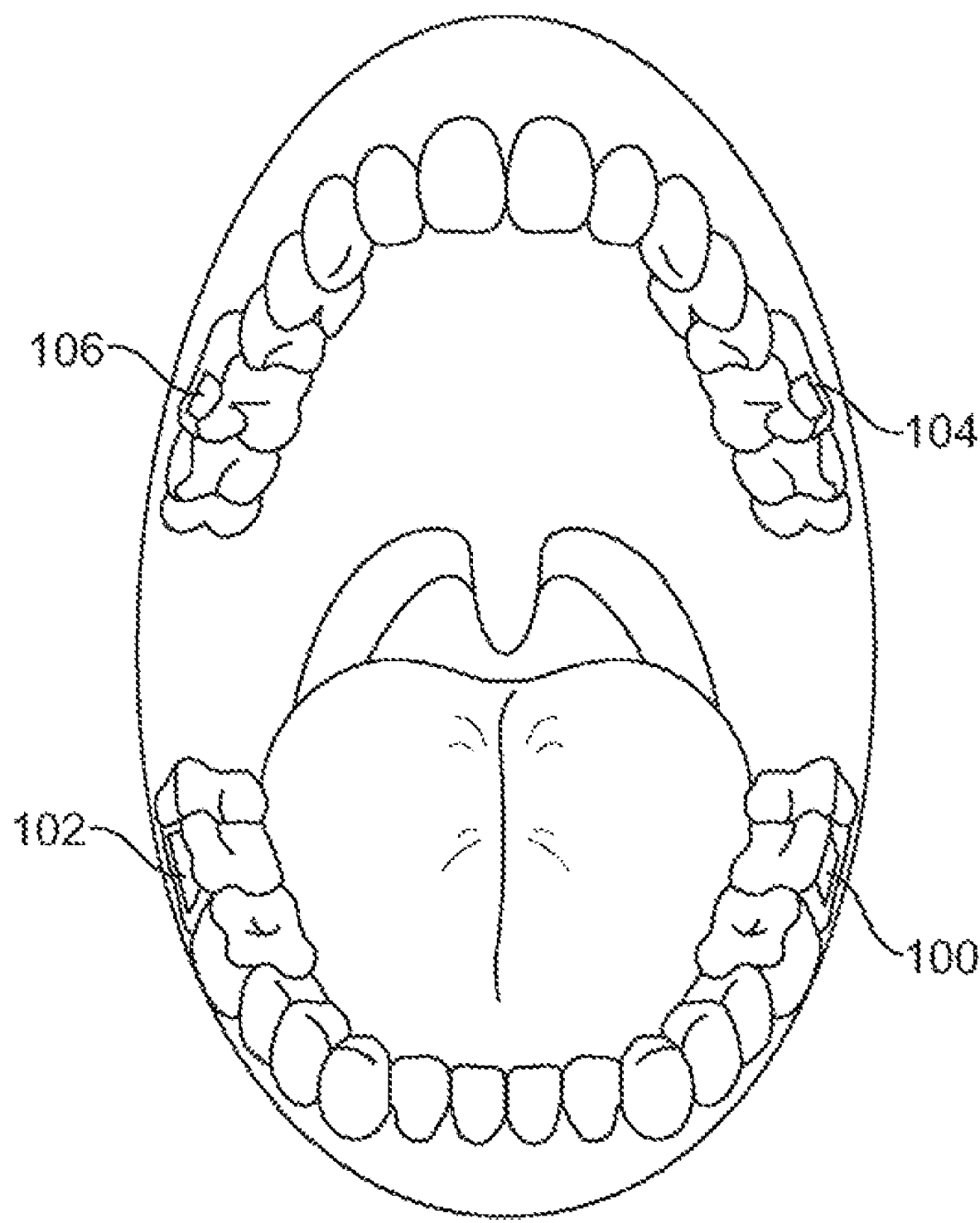
FIG. 9 shows yet another variation illustrating at least one microphone and optionally additional microphone units-positioned around the user's mouth and in wireless communication with the electronics and/or actuator assembly.

In yet another variation for separating the microphone from the actuator assembly, FIG. 9 illustrates another variation where at least one microphone 102 (or optionally any number of additional microphones 104, 106) may be positioned within the mouth of the user while physically separated from the electronics and/or actuator assembly 100. In this manner, the one or optionally more microphones 102, 104, 106 may be wirelessly or by wire coupled to the electronics and/or actuator assembly 100 in a manner which attenuates or eliminates feedback from the actuator, also described in further detail below.

In utilizing multiple actuators and/or processing units, several features may be incorporated with the oral appliance(s) to effect any number of enhancements to the quality of the conducted vibrators signals and/or to emulate various perceptual features to the user to correlate auditory signals received by a user for transmitting these signals via bone conduction through teeth or bone structures in and/or around the mouth. Examples of various processing methods and systems for simulating directionality as well as for processing algorithms for filtering out undesirable signals, among other features, are shown and described in further detail in U.S. patent application Ser. No. 11/672,239 filed Feb. 7, 2007, which is incorporated herein by reference in its entirety. The features shown and described mats be utilized with any of the variations described herein and in any number of combinations as practicable.

Figure 10:
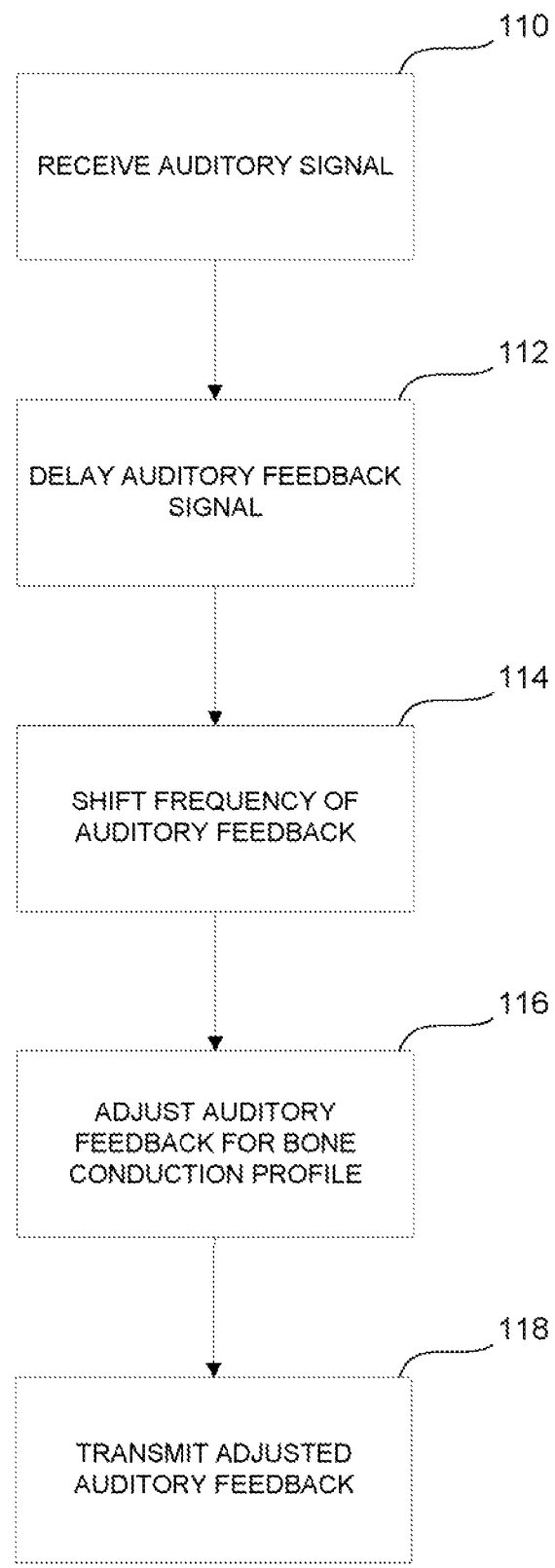
FIG. 10 illustrates a flowchart of an optional treatment for altering a user's voice to be retransmitted back to the user through bone conduction via the removable oral appliance.

In using any of the variations of the oral appliance assembly described herein, the oral appliance may utilize AAF for the treatment of stuttering, as illustrated in one example in the flow chart of FIG. 10. Accordingly, in one example of treating stuttering via DAF and FAF, the user's own voice may be received via a microphone 100 located upon the oral assembly or separately from the oral appliance. The user's voice may then be processed, e.g., by processor 54, such that the voice data is delayed 112 by about, e.g., 60 ms. The delay in the auditory feedback may alternatively range anywhere from about 50 ms to 200 ms.

In addition to delaying the auditory feedback, the auditory feedback signal may also be shifted in frequency 114 by about, e.g., +500 Hz. In other variations, the frequency may be shifted anywhere from less than a half octave to a full octave or more, depending upon the desired results. With the auditory feedback delayed and shifted in frequency, the signal may be further adjusted or equalized to account for the user's particular bone conduction profile 116, which may be obtained utilizing standard bone conduction measurements. Accounting for the user's bone conduction profile, particularly through the skull, may facilitate optimization of the altered auditory feedback signal by adjusting particular frequencies or adjusting amplitude or gain such that the vibrationally conducted altered feedback signal reaches the user's middle and/or inner ear with minimal loss.

Once the altered feedback signal has been appropriately adjusted for delay, frequency, bone conduction, etc., it may be vibrationally transmitted via the removable oral appliance 118 through the user's tooth or teeth or other bone structure such as the palatal or mandibular bone, etc. Thus, as the user speaks their voice is sampled and adjusted, as described above, and then retransmitted via the removable oral appliance to effect AAF treatment and to reduce or eliminate stuttering.

In other variations, rather than utilizing both DAF and FAF in altering the auditory feedback signal, DAF treatment may be utilized alone, as illustrated in the flowchart of FIG. 11A. In this example, the user's voice signal 110 may be delayed 112, as above by 60 ms or anywhere from 50 ins to 200 ms. The delayed auditory feedback signal may then be further adjusted to account for the user's bone conduction profile 116 and then the resulting feedback signal may be transmitted via vibrational conduction 118 through the removal oral appliance. In yet another variation, rather than utilizing DAF treatment, FAF treatment may be utilized alone, as illustrated in the flowchart of FIG. 11B. In this case, the user's voice signal 110 may be shi fled in frequency 114 by, e.g., +500 Hz, and then further adjusted for the user's bone conduction profile 116 and then transmitted via vibration conduction 118 through the removal oral appliance. In these and other examples, adjustment of the user's auditory feedback signal by their (or a standard) bone conduction profile 116 may be performed prior to adjustment of the delay or frequency shift.

Figure 12:
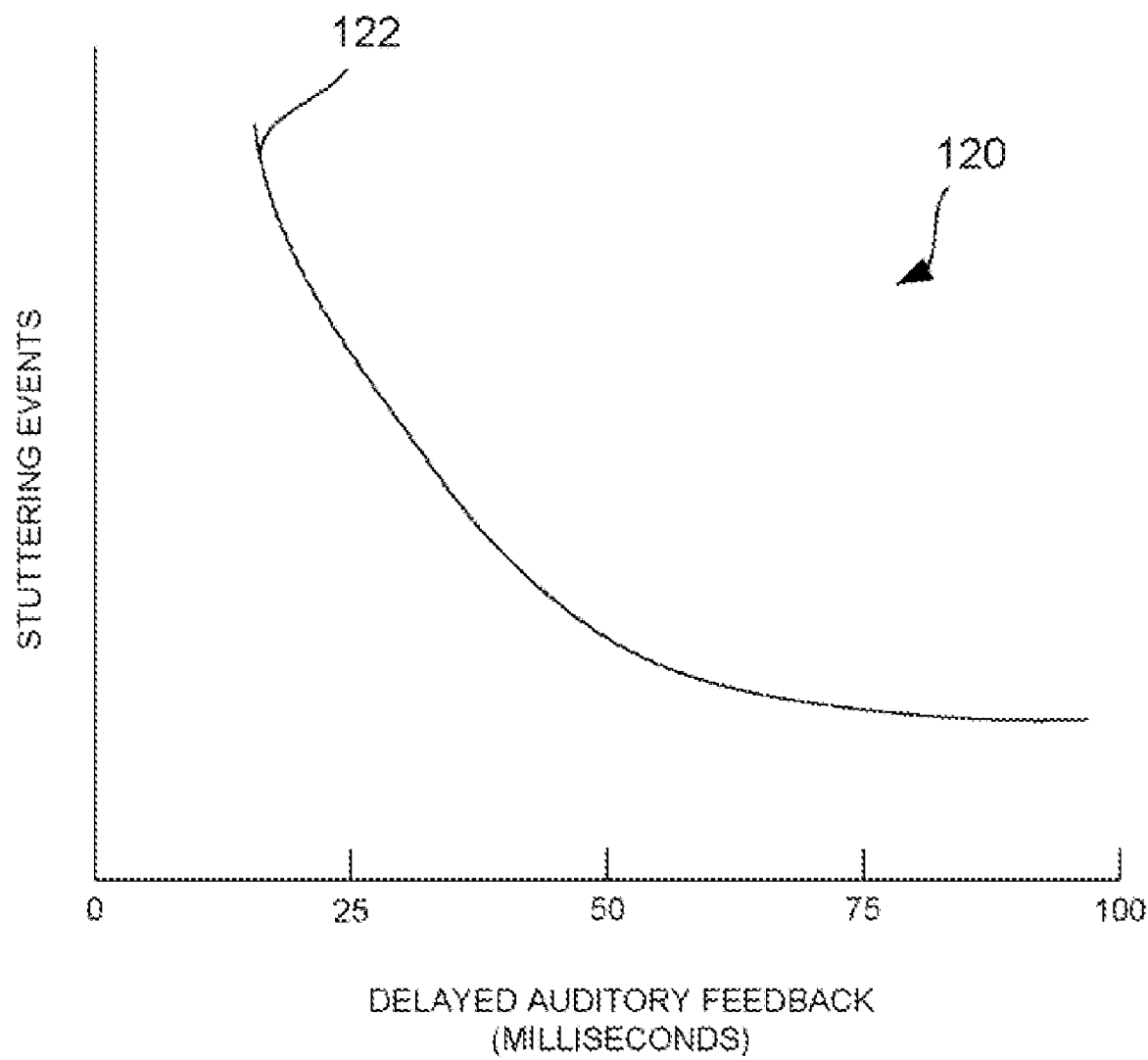
FIG. 12 illustrates a graph indicating a correlation between an increase in the delay of the auditory feedback and the number of stuttering events.

In determining the amount of delay to adjust the auditory feedback signal, it may be delayed anywhere from about 50 ms to 200 ms, as mentioned above. As shown in chart 120 in FIG. 12, curve 122 illustrates the relationship between an increase in delayed auditory feedback (in milliseconds) and a reduction in the number of stuttering events from the speaker. Generally, as the amount of delay in the auditory feedback is increased, the number of stuttering events decreases exponentially, particularly delay times of 25 ms or greater.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method for treating stuttering, comprising:
providing an oral appliance comprising a housing and an actuatable transducer disposed within or upon the housing;
positioning the housing onto the at least one tooth, wherein the housing is configured to engage the at least one tooth without requiring anatomical modification of the at least one tooth and without bonding to the at least one tooth, wherein the appliance produces an interference fit between the appliance and at least two surfaces of the at least one tooth;
receiving an audio signal of a voice of the patient;
introducing a time delay in the audio signal of the patient's voice to generate an altered audio feedback signal; and
vibrationally conducting the altered audio feedback signal from the oral appliance to a surface of the at least one tooth whereby stuttering by the patient is diminished.

2. The method of claim 1 wherein receiving an audio signal comprises sampling the audio signal via one or more microphones within the oral appliance.

3. The method of claim 1 wherein introducing a time delay comprises introducing the time delay via a processor in communication with the oral appliance.

4. The method of claim 3 wherein the processor is integrated within the oral appliance.

5. The method of claim 3 wherein the processor is separated from the oral appliance.

6. The method of claim 3 wherein introducing the time delay comprises delaying the audio signal of the patient's voice from 50 ms to 200 ms.

7. The method of claim 1 further comprising shifting a frequency of the audio signal prior to vibrationally conducting the altered audio feedback signal.

8. The method of claim 7 wherein shifting a frequency comprises shifting the frequency by 500 Hz.

9. The method of claim 1 further comprising adjusting the altered audio feedback to accommodate a bone conduction profile of the patient prior to vibrationally conducting the altered audio feedback signal.

10. The method of claim 1 wherein vibrationally conducting comprises further conducting through a palatal bone of the patient via the oral appliance.

11. The method of claim 1 further comprising removing the oral appliance from patient.

12. A stuttering treatment apparatus, comprising:
a housing that is configured to engage at least a portion of at least one tooth of a patient without requiring anatomical modification of the at least one tooth and without bonding to the at least one tooth, wherein the apparatus produces an interference fit between the apparatus and at least two surfaces of the at least one tooth;
a processor positioned within or along the housing, wherein the processor is configured to introduce a time delay in an audio signal of a voice of the patient to generate an altered audio feedback signal; and
an actuator disposed within or upon the housing and configured to transmit vibrations to a surface of the at least one tooth such that the actuator conducts the altered audio feedback signal whereby stuttering by the patient is diminished.

13. The apparatus of claim 12 further comprising one or more microphones in communication with the processor for receiving the audio signal of the voice of the patient.

14. The apparatus of claim 12 wherein the processor is configured to introduce a time delay of 50 ms to 200 ms.

15. The apparatus of claim 12 wherein the processor is further configured to shift a frequency of the audio signal of the voice.

16. The apparatus of claim 15 wherein the processor is configured to shift the frequency by 500 Hz.

17. The apparatus of claim 12 wherein the processor is further configured to adjust the audio feedback to accommodate a bone conduction profile of the patient.

18. The apparatus of claim 12 wherein the housing is removable from the at least one tooth.

19. The apparatus of claim 12 further comprising an external controller in wireless communication with the processor.

* * * * *